United States Patent [19]
Lin et al.

[11] Patent Number: 5,306,637
[45] Date of Patent: Apr. 26, 1994

[54] METHOD FOR RECOVERY OF INTRACELLULAR MATERIAL BY DISRUPTION OF MICROBIAL CELLS WITH CARBON DIOXIDE UNDER PRESSURE

[76] Inventors: Ho-Mu Lin, 30 Morehouse Ct.; Li-Fu Chen, 112 Seneca La., both of West Lafayette, Ind. 47906

[21] Appl. No.: 58,671

[22] Filed: May 10, 1993

Related U.S. Application Data

[63] Continuation of Ser. No. 748,435, Aug. 22, 1991, abandoned.

[51] Int. Cl.$^5$ .............. C12N 1/06; C12N 9/36; C12N 9/88
[52] U.S. Cl. .................... 435/259; 435/41; 435/71.1; 435/71.2; 435/206; 435/224; 435/232
[58] Field of Search ............... 435/41, 71.1, 71.2, 435/224, 232, 259, 206

[56] References Cited

U.S. PATENT DOCUMENTS

| | | | |
|---|---|---|---|
| 648,468 | 5/1900 | Ruckforth | 435/259 |
| 2,319,831 | 5/1943 | Torrington | 435/259 |
| 3,716,452 | 2/1973 | Kitamura et al. | 435/259 |
| 3,816,260 | 6/1974 | Sugiyama | 435/259 |
| 3,890,198 | 6/1975 | Kobayashi et al. | 435/259 |
| 4,481,294 | 11/1984 | Downs | 435/259 |
| 4,795,709 | 1/1989 | Hopkins | 435/259 |

FOREIGN PATENT DOCUMENTS

| | | | |
|---|---|---|---|
| 8702697 | 5/1987 | World Int. Prop. O. | |
| 9101367 | 2/1991 | World Int. Prop. O. | 435/259 |

*Primary Examiner*—Herbert J. Lilling
*Attorney, Agent, or Firm*—Cushman, Darby & Cushman

[57] ABSTRACT

This invention is a method to rupture microbial cells in order to recover intracellular material in the cells comprising:
a) treating the cells with carbon dioxide under pressure sufficient to enter the cells for time sufficient to allow enough carbon dioxide into the cells to effect later rupture, then
b) suddenly releasing the applied fluid pressure on the cells so that the outer wall or membrane of the cells is ruptured by the expansion of carbon dioxide within the cell. Preferably the remaining intracellular material of the cells is separated and recovered. Also the treatment can be in conjunction with lytic enzyme to increase rupture rates. Preferably the enzyme remains active and protein in the cells retains its native state in the ruptured cell suspension. The preferred time for treating is from between about one hour and about fifteen hours. It is also preferred to treat initially at a pressure of from above about 500 psi gage to about 5000 psi and a temperature of about 10° to about 85° C. For improved rupture efficiency, the treating is repeated at least once.

5 Claims, 9 Drawing Sheets

METHOD FOR RECOVERY OF INTRACELLULAR MATERIAL BY DISRUPTION OF MICROBIAL CELLS WITH CARBON DIOXIDE UNDER PRESSURE

This is a continuation of application Ser. No. 07/748,435, filed on Aug. 22, 1991, which was abandoned upon the filing hereof.

BACKGROUND OF THE INVENTION

1. Field of the Invention

This invention relates to a method for recovery of intracellular material by disruption of microbial cells with carbon dioxide under pressure.

2. Background Art

Microbial cells have long been recognized as an important source of commercially useful biochemicals, antibiotics, food and enzymes. With increasing demand of microbial products in industry and medicine, considerable efforts have recently been committed to develop technologies for production of intracellular microbial materials from microorganisms and various genetically altered cultures. Release of cell contents is also vital to many investigations of bacterial metabolism. In any case, the cell disruption is a necessary operation for recovery or isolation of protein, intracellular enzymes and organelles. A variety of disruption techniques had been developed, and some are available commercially. Mechanical methods appear to be favored at the present time by their economic advantages, although several non-mechanical methods, particularly the enzymatic lysis, have attracted great attention. However, many of these methods often degrade or denature proteins in the process.

Yeast is the most widely accepted traditional food item which has been exploited as a potential protein source; however, despite its nutritional value and abundant supply, the potential of yeast as a major food source has been hampered by various problems. Ideally, yeast cell biomass should be consumed directly as food or as food ingredients, but the thick cell wall reduces the digestibility and bio-availability of protein. The cell wall substances often cause allergic responses, diarrhea, and flatulence. Even after the cell wall is removed, some lipid components contribute to off-flavors by oxidation, and more importantly, the functional properties of proteins are impaired in the process. Finally, the protein from single cells contains a high level of nucleic acids, which can cause uricacidemia and gout.

The nature of the cell walls and their removal have been discussed in the literature. Autolysis (particularly, thio-activated autolysis) and enzymatic lysis are among the conventional techniques in wide use for disintegration of microbial cells, other than yeast, to recover intracellular enzymes. Although most microbial cell walls can readily be ruptured, yeast cell walls are very difficult to disintegrate. Selection of yeast strains with weaker cell walls and alkaline treatment can facilitate yeast protein recovery. Other methods, such as homogenization, freeze-thawing, and pressurization have been used to rupture the yeast cells.

Among these methods, pressurization may be the least expensive if the pressure can be kept at a reasonably low range. Prior investigation of gas pressure for rupturing cells, but not yeast cells, has found that carbon dioxide was effective at 500 psi.

Supercritical fluid (SCF) has recently demonstrated great potential in its applications to food and pharmaceutical industries. The fluid possesses a combination of "gas-like" and "liquid-like" properties. It penetrates like a gas, and functions like a liquid. Such unique characteristics of SCF have found broad applications in diverse areas, particularly for extraction and separation of natural products. Various prior studies have extensively applied SCF as a medium, in place of conventional solvents, in enzyme reactions.

SUMMARY OF THE INVENTION

This invention is a method to rupture microbial cells in order to recover intracellular material in the cells comprising:

a) treating the cells with carbon dioxide under pressure sufficient to enter the cells for time sufficient to allow enough carbon dioxide into the cells to effect later rupture, then b) suddenly releasing the applied fluid pressure on the cells so that the outer wall or membrane of the cells is ruptured by the expansion of carbon dioxide gas within the cell. Preferably the remaining intracellular material of the cells is separated and recovered. Also the treatment can be in conjunction with lytic enzyme to increase rupture rates. Preferably the enzyme remains active and protein in the cells retains its native state in the ruptured cell suspension.

The preferred time for treating is from between about one hour and about twelve hours. It is also preferred to treat initially at a pressure of from above about 500 psi gage to about 5000 psi and a temperature of about 10° to about 85° C. For improved rupture efficiency, the treating is repeated at least once. Also the carbon dioxide can contain an entrainer to enhance the rupture efficiency. The entrainer can be selected from a group consisting of chemicals such as ethanol, ethylene, toluene and mixtures thereof. It is preferred in this method to have lytic enzyme, which hydrolyzes cell wall material, present in the cells. Examples of lytic enzymes are $\beta$-glucuronidase, lysozyme, or glucanases. The lytic enzyme and the entrainer can both be present in or with the carbon dioxide or like fluid.

Finally it is also expected that carbon dioxide can be replaced by a fluid selected from the group consisting of ethylene, ethane, propylene, propane and mixtures thereof in the process of this invention.

This invention extends the application of SCF to a new area in which the SCF is used for disruption of microbial cells to produce protein. The technique is beneficial to yeast cells in particular, because the SCF is capable of extracting off-flavors and, possibly, nucleic acids in the process of cell disintegration.

Although other fluids can be used, carbon dioxide was chosen in this work as a primary SCF because it is non-toxic, non-flammable, inexpensive and physiologically safe. The critical temperature of carbon dioxide (31.1° C.) is just above ambient, which minimizes the problems of thermal degradation (or denaturation) of delicate biological materials and natural products. In addition, its phase behavior and other thermophysical properties that are needed for process analysis and development are well studied.

The method of this invention differs from prior methods, inter alia, by rupturing microbial cells by the sudden release, optionally repeatedly, of the applied fluid pressure. This causes the fluid (SCF) in the cells to "pop" the cell walls. Release of the process pressure involves a sudden release of the applied fluid pressure which follows penetration of SCF into cells. The expansion of SCF within the cells when it is released (depressured) forces the breakage of microorganisms. It is simple, inexpensive, and, more importantly, non-injurious to enzyme activities. The functional properties of proteins are all preserved. Disruption rates are sensitive to such process variables as temperature, pressure, and addition of entrainers to the fluid. Under optimum conditions, over 80% of cell walls can easily be ruptured within an hour for a variety of microbial cells. The disruption is, however, not as effective for some other cells. A typical example is yeast cells, which have been described as one of the most robust and rigid of all microbial cell walls. However, this invention does disrupt yeast cells.

DESCRIPTION OF PREFERRED EMBODIMENTS

Example I

Microorganism

Cells of *Saccharomyces cerevisiae* were purified from baker's yeast (Red Star) on YMP agar (DIFCO Laboratories, Detroit, Mich.) plates containing yeast extract (0.3% w/v), malt extract (0.3% w/v), bacto-peptone (0.5% w/v) and glucose (2% w/v). The purified yeast was maintained on a YMP agar slant as a stock culture. Cells were first transferred from slants to a 500 mL flask containing 200 mL liquid YMP medium which contains 10% (w/v) glucose. The cultures were incubated at 30° C. in a shaker with agitation (200 rpm). Fresh cultures were prepared daily with the same procedure. After 18 hours of incubation, the yeast cells were harvested and washed with distilled water. After the liquid was decanted, the pellets were ready for subsequent experiments.

Carbon dioxide was purchased from Matheson Gas Products with a minimum purity of 99.99%.

Apparatus

A static apparatus was used in this work which consisted of two major components: a piston injector and a pressure vessel. Carbon dioxide was supplied from the gas cylinder to a Ruska pump (Model 2200, Ruska Instrument Corp., Houston, Tex.), which compressed $CO_2$ to a desired pressure prior to injection into the pressure vessel. The design of the vessel was similar to that of the Kuentzel closure reactor vessel (Series KC single ended unit) of Autoclave Engineers, Inc., (Erie, Pa.) with an internal volume of approximately 6.6 mL. Another pressure vessel of 50mL internal volume (Model 1019 HC, Parr Instrument Co., Moline, Ill.) was also used to investigate the effects of excessive amounts of $CO_2$ on cell disintegration. The vessel was rated at a maximum pressure of 2,200 psi at 40° C. The vessels and all other parts exposed to high pressures were made of stainless steel 316. A thermostated water bath was used to maintain the pressure vessel at experimental temperature. A pressure gauge was installed in the $CO_2$ inlet of the vessel to read the pressure.

Cell Disruption

To start an experiment, one gram of wet cells was placed in the pressure vessel, and 1 mL Tris-HCl buffer solution (pH 7.0 and 0.05M) was added. In some experiments, 10 mg of $\beta$-glucuronidase (EC 3.2.1.31, from *Helix pomatia* supplied by Sigma Chemical Co., St. Louis, Mo.) or 1 mL toluene was also added to the suspension. The vessel was then enclosed and immersed in the thermostated water bath at the experimental temperature (25°, 35° or 55° C.). The yeast cells in the vessel were agitated with a magnetic stirrer. After the temperature was equilibrated and all tubing connections were secured, carbon dioxide was injected into the vessel at a fixed pressure (1,000, 3,000, or 5,000 p.s.i.) via a preheated or cooling coil. The yeast cells were exposed to carbon dioxide for a designated length of time. Carbon dioxide was then rapidly released, and 4 mL of Tris-HCl was immediately added to the vessel after it was opened. The cell suspension was centrifuged and the supernatant assayed for total protein and enzyme activities.

Enzyme Assay

Activity of yeast alcohol dehydrogenase (EC 1.1.1.1) was determined by the method of Vallee and Hoch in Proceedings of Nat'l Academy of Sciences, 41(6), p.327 (1955). Invertase (EC 3.2.1.26) was assayed by adding 0.1 mL of 0.125M sucrose to 0.9 mL supernatant. The pH of the supernatant was adjusted to 4.5 by adding 0.1N HCl. The reaction was carried out for 3 minutes, and followed by heating the reacted solution at 100° C. in a water bath for 5 minutes. Glucose formation in the solution was measured by a Beckman Glucose Analyzer. One unit of invertase is defined as the enzyme which hydrolyses 1 micromole of sucrose in 1 minute at 55° C. and pH 4.5. The activity of glucose-6-phosphate dehydrogenase (EC 1.1.1.49) was determined by the method of DeMoss, Methods in Enzymology Vol.1 p.328 (1955). The method for determination of fumarase (EC 4.2.1.2) activity was described by Racker in Biochimica Et Biophysica Acta, 4,211(1950), except that Tris buffer (pH 7.0, 0.05M) replaced phosphate buffer. The concentration of protein was estimated by Lowry's method, J. Biol. Chem. 193, 265 (1965), with bovine serum albumin as a standard.

Results and Discussion

The experiments were performed in both regions of subcritical and supercritical temperatures of carbon dioxide over the pressure range of 1000–5000 psi. Experimental results in two different regions of temperature are presented separately in the Figures, described below.

Carbon Dioxide at Subcritical Temperatures

Figure 1:
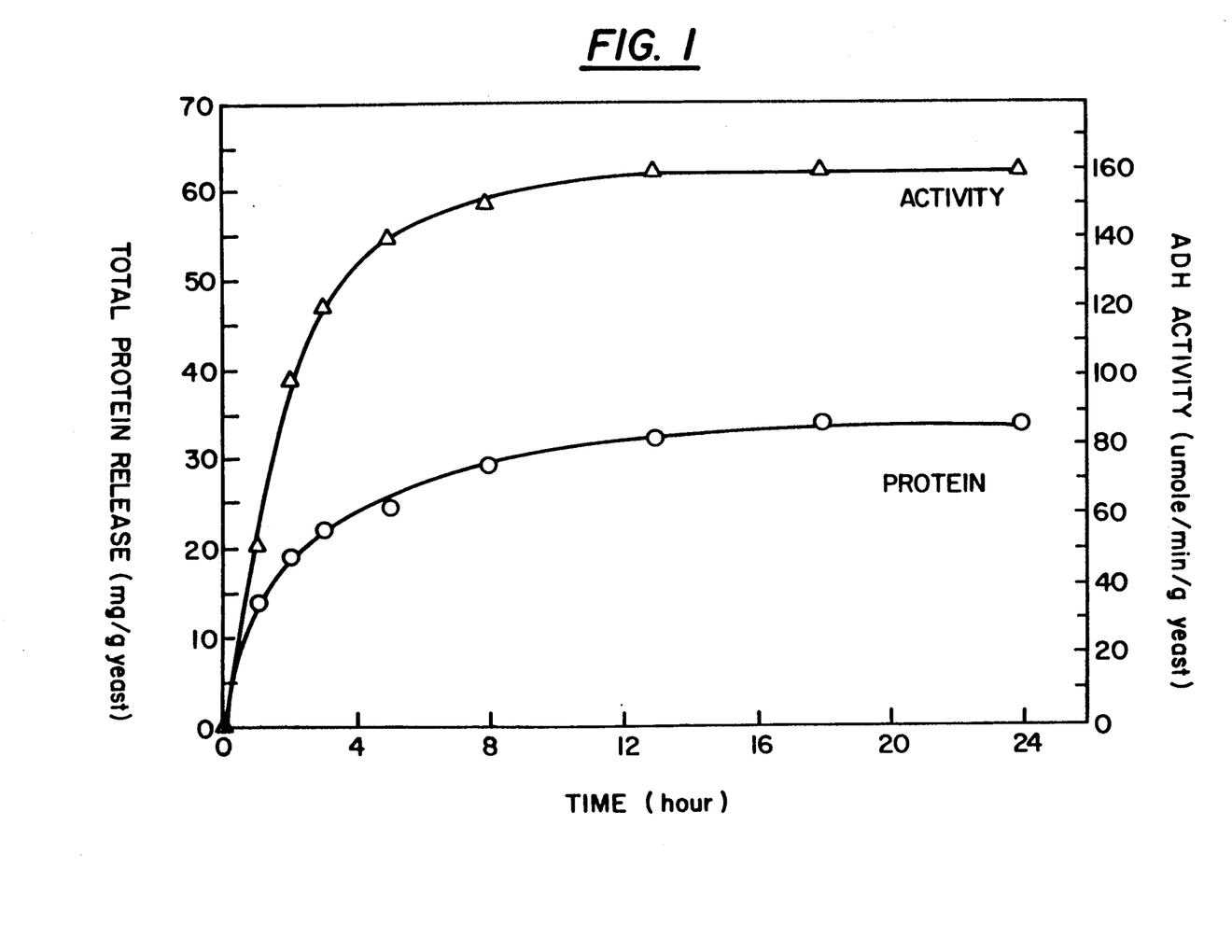
FIG. 1 is a set of two curves which show release of total proteins from yeast and ADH activity over time for experimental results using carbon dioxide at the subcritical temperature of 25° C. and 1,000 p.s.i.
Figure 2:
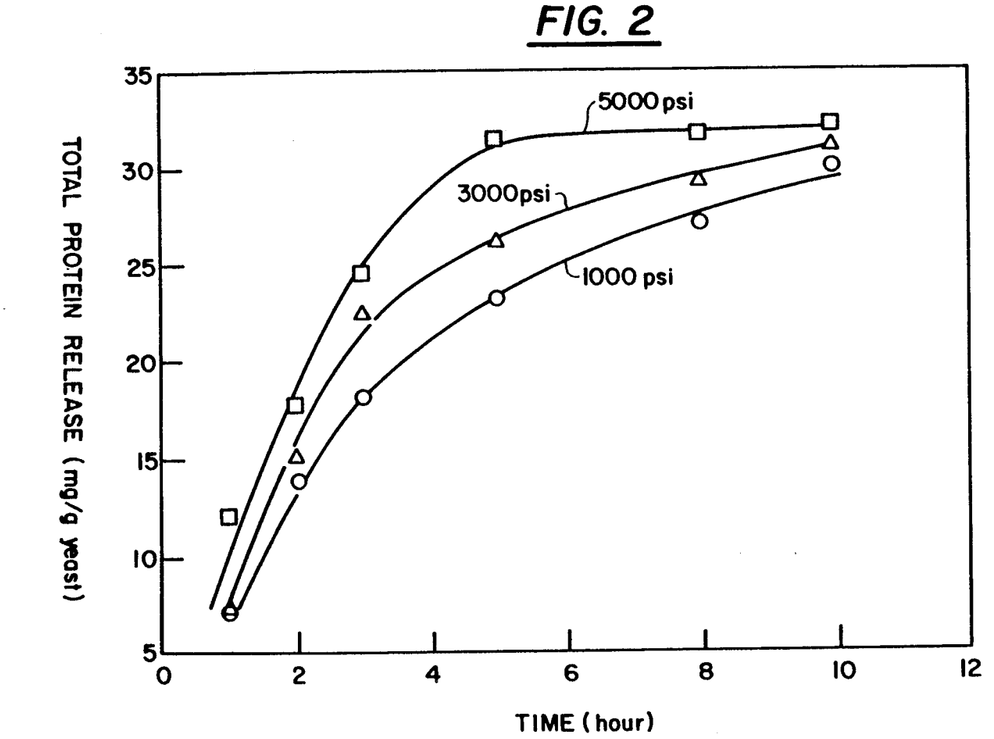
FIG. 2 is a set of curves showing total protein release from yeast at the three pressures shown and 25° C.

Experimental results were obtained at 25° C. FIG. 1 shows the release of the soluble protein and the activity of alcohol dehydrogenase (ADH) as a function of disruption time at the experimental pressure of 1,000 psi. In 15 hours, one gram (wet weight) of yeast cells released approximately 33 mg of soluble protein, which contained 160 units of alcohol dehydrogenase. By prolonging the disruption time to 24 hours, neither an increase nor a decrease in the amount of protein release and enzyme activity of alcohol dehydrogenase was observed. At higher $CO_2$ pressures, the length of disruption time to release maximal quantity of protein was significantly reduced, as indicated in FIG. 2. The maximal amount of protein release at 3,000 and 5,000 psi of $CO_2$ occurred at 12 and 5 hours, respectively, while the activities of ADH were preserved at about 160 units per gram of yeast cells.

Figure 3:
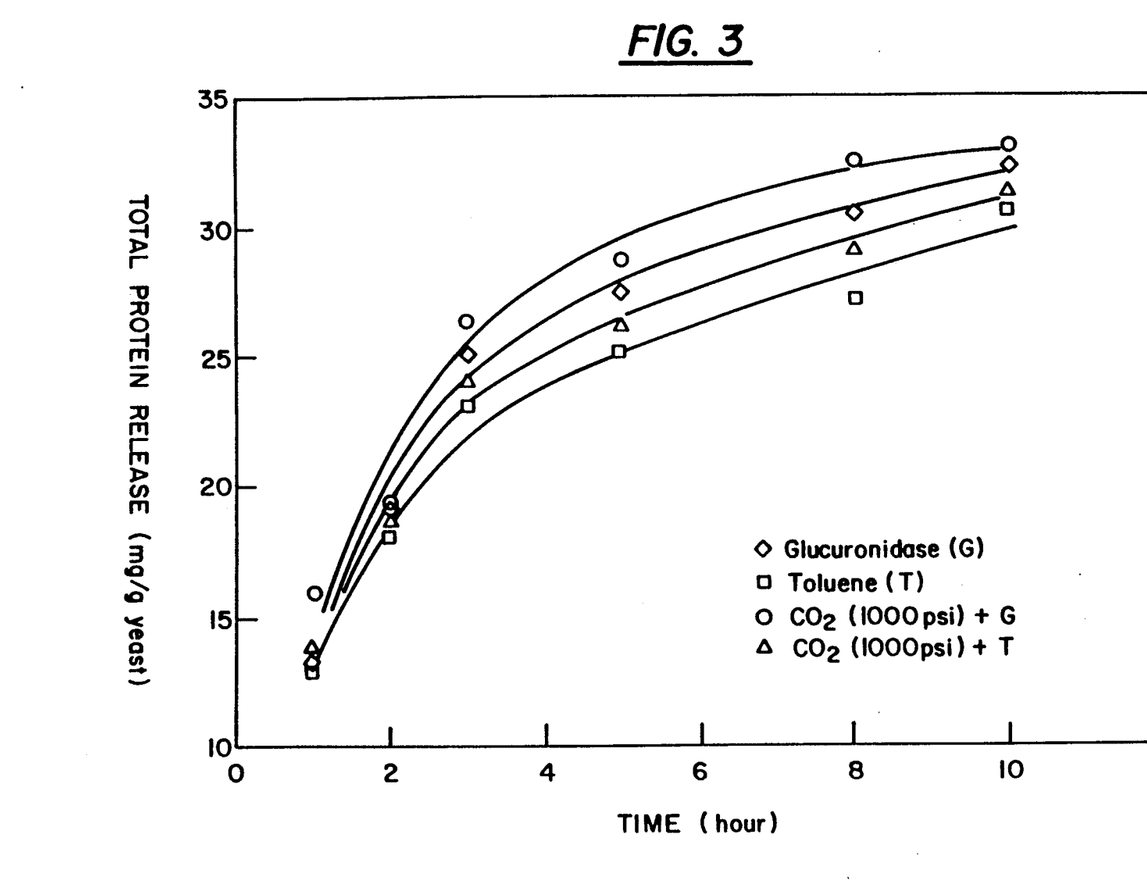
FIG. 3 is a set of curves showing the effect of glucuronidase, toluene at atmospheric pressure and each combined with carbon dioxide at 1,000 p.s.i., all at 25° C.

In a preliminary experiment, the same baker's yeast cells were disrupted by grinding them at 25° C. with abrasive glass. The whole process was completed within one hour with a maximal amount of 33 mg of protein released from one gram of wet yeast cells. Although the mechanical method could disrupt yeast cells more efficiently than high-pressure $CO_2$, the activity of alcohol dehydrogenase diminished to 100 units per gram of yeast cells. The loss of enzyme activity was expected, since no reducing agent or protease inhibitors were added in the rupturing process. Intensive localized heating effects in the process of mechanical disruption also often ensue with enzyme denaturation. Other disruption methods were also performed in this work for the yeast cells. FIG. 3 compares the rates of protein release by autolysis at atmospheric pressure with toluene and by enzymatic lysis with $\beta$-glucuronidase. Both methods released about the same amount of protein as fast as high pressure $CO_2$, but a significant loss of alcohol dehydrogenase activity was found. Results from 1,000 psi $CO_2$ with addition of 1 mL toluene or 10 mg $\beta$-glucuronidase (to 1 g of yeast cells) are also shown in the figure for comparison. The effects of adding toluene and $\beta$-glucuronidase on the rates of disruption became even more apparent at higher pressures of $CO_2$, as will be discussed later. The results demonstrate that the presence of $CO_2$ in the disruption process preserves the activities of alcohol dehydrogenase. The mechanism of this enzyme stabilization is under investigation; however, there are several possible explanations: (1) $CO_2$ may alter the hydrophobicity of the environment which inhibits protease. It was reported that during the lysis of *Schizosaccharomyces pombe* with $\beta$-glucuronidase, addition of protease inhibitor prevented the loss of xylose isomerase; and (2) under high pressures, dissolved $CO_2$ lowers the pH value to where protease cannot function. Regardless of these postulations, this disruption method with $CO_2$ can be a valuable technique to produce enzymes from yeast, if other enzymes can also be preserved.

Figure 4:
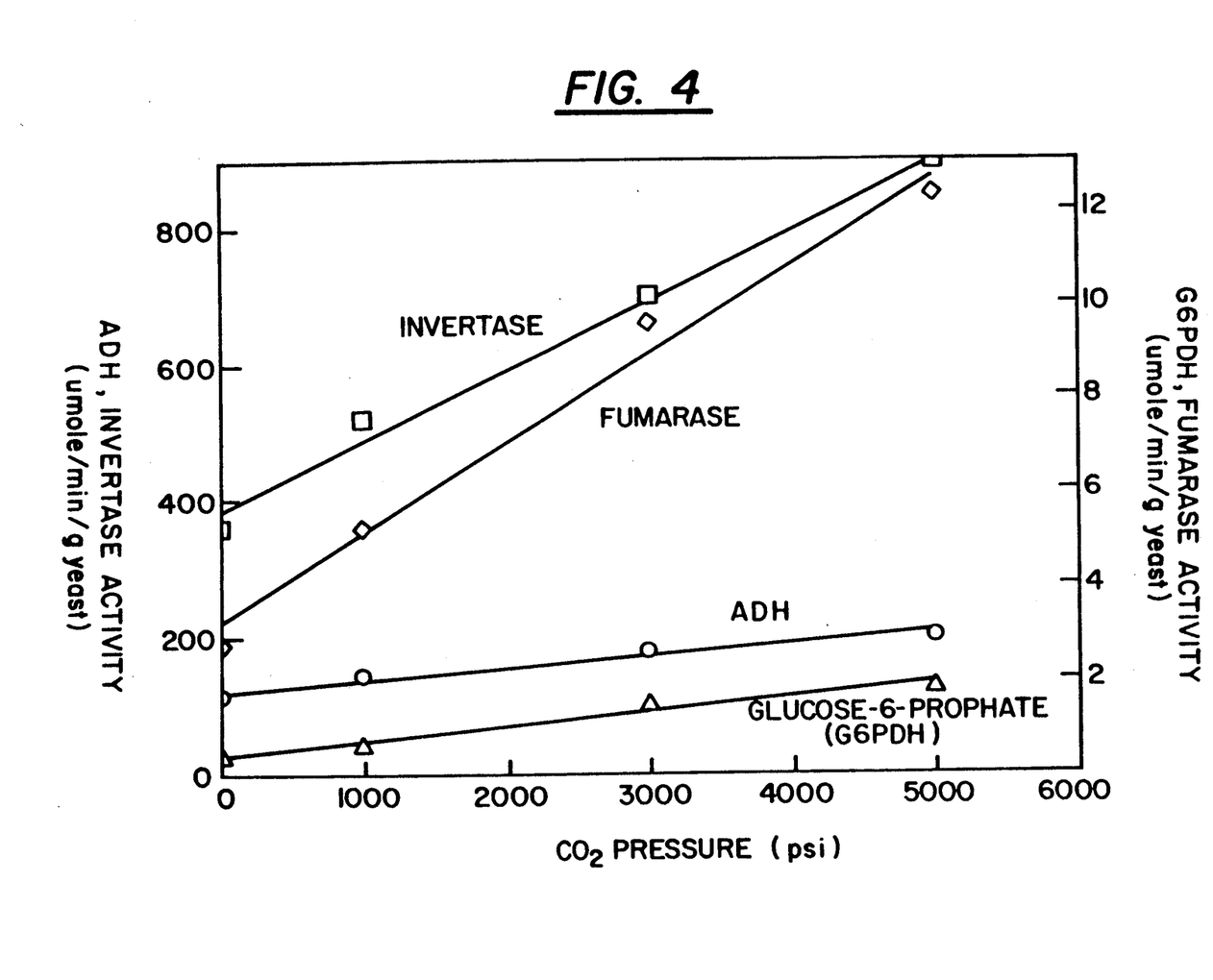
FIG. 4 is a set of curves showing enzyme activities of ADH (alcohol dehydrogenase), invertase, glucose-6-prophate, and fumarase at various carbon dioxide pressures at 25° C. The yeast cell sample contained $\beta$-glucuronidase.

In addition to alcohol dehydrogenase, three other enzymes were assayed after cells were disrupted by high pressure $CO_2$ with $\beta$-glucuronidase. These were invertase, glucose-6-phosphate dehydrogenase, and fumarase which are located in different compartments of the yeast cell. When the pressure of $CO_2$ was at 5,000 psi in the presence of $\beta$-glucuronidase, these enzymes were released to their maximal levels in 90 minutes. FIG. 4 shows the activity of each released enzyme after two-hour exposure under various pressures. In this Figure (and in all Figures) "ADH" means alcohol dehydrogenase. At zero pressure, which corresponds to enzymatic lysis with $\beta$-glucuronidase, the activity of each enzyme is lower than that under high pressure $CO_2$. Similar results were obtained when autolysis in toluene and mechanical grinding with abrasive glass were employed to disrupt yeast cells. In all cases, the activities of these enzymes were enhanced under high pressure $CO_2$.

To examine the effects of excessive amounts of $CO_2$ on the disruption, experiments were repeated at same conditions of pressure and temperature with a 50 mL vessel. No significant differences were found if the cell suspension was stirred in the course of disruption.

Carbon Dioxide at Supercritical Temperatures

Figure 5:
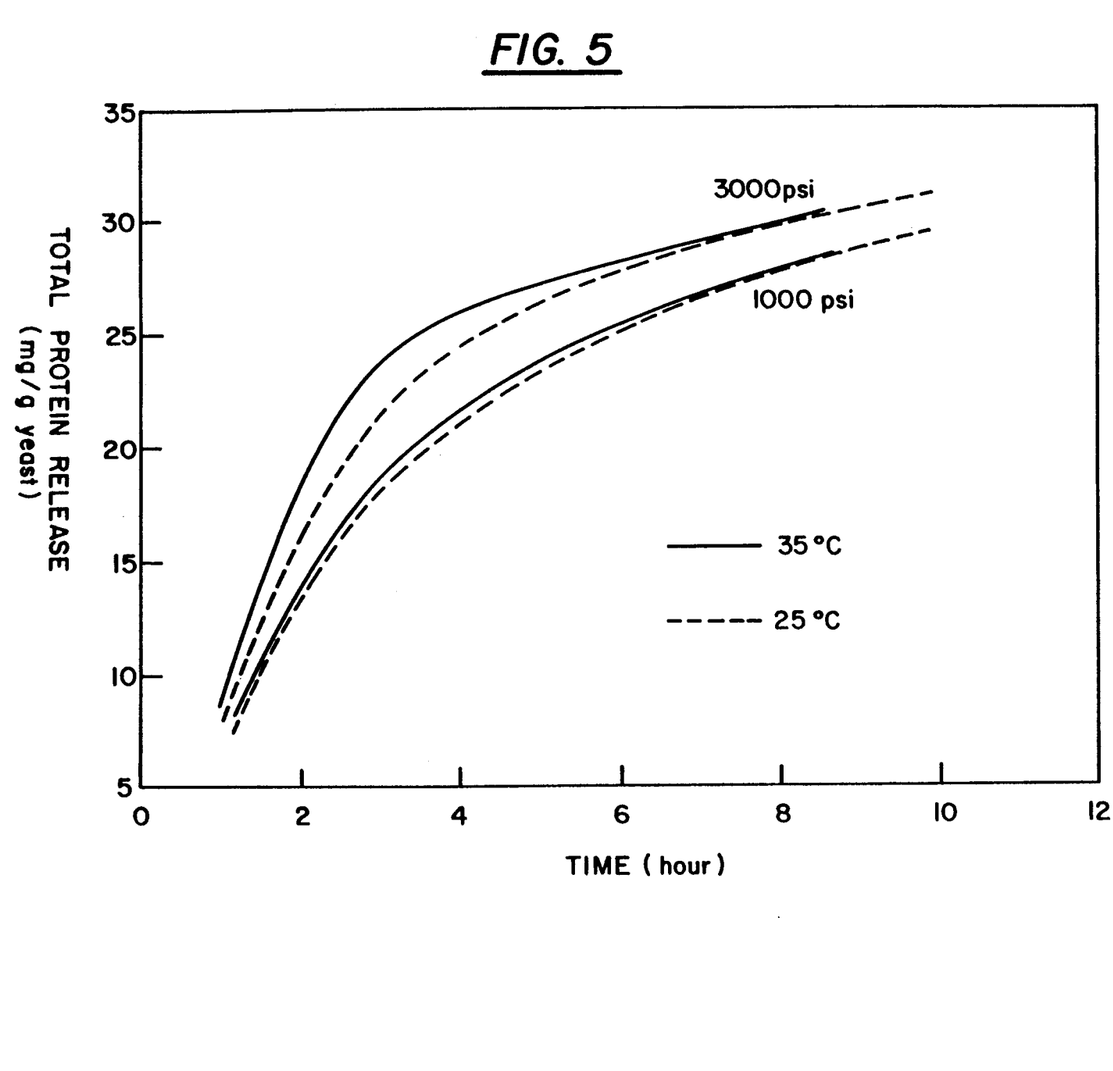
FIG. 5 is a set of curves which show the effect of temperature and pressure when using carbon dioxide to release protein from yeast.

Two temperatures (35° and 55° C.) were studied in the supercritical region of $CO_2$. FIG. 5 compares experimental results of total protein release at 35° C. with those at 25° C. The temperature effects are not evident under $CO_2$ pressure of 1,000 p.s.i. However, protein release appears to approach its maximal amount at a significantly faster rate with supercritical $CO_2$ at higher pressures. The activities of released enzymes were again preserved in the presence of $CO_2$, without addition of reducing agents and protease inhibitors which are commonly used in the disruption process. The discussion presented earlier with subcritical $CO_2$ is applicable to this temperature and, therefore, need not be elaborated.

The enzyme activities began to decay at higher temperatures (>35° C.) and were almost completely lost at temperatures of above 55° C., although the rates of protein release were sequentially improved with increments in temperature.

Using high pressure $CO_2$ to lyse microorganisms for recovery of intracellular protein in combination with cell lytic enzymes is a part of this invention. The phenomenon that pressurized $CO_2$ can prevent the deactivation of the released enzymes in the presence of crude preparations of cell lytic enzymes may reduce the cost of protein isolation from single cells. Furthermore, it was observed that $CO_2$ may have extracted the off-flavors from the ruptured cell suspensions, and the off-flavor compounds were removed when $CO_2$ were released.

EXAMPLE 2

This work demonstrates a method to improve the disruption rates of cells by repeatedly releasing the applied fluid pressure within the cells in the midst of a disruption process. The effectiveness of this technique is illustrated by the experimental results of rupturing yeast cells, which have been described as having one of the most robust and rigid of all microbial cell walls. The same technique can be analogously applied to other microbial cells.

Experimental

Cells of *Saccharomyces cerevisiae* used in this work were purified bakers' yeast from Red Star. The preparation of yeast samples was detailed in Example 1. The yeast pellets of this work contain 10% less moisture than those used in Example 1. Carbon dioxide was purchased from Matheson Gas Products with a minimum purity of 99.99%.

The apparatus of Example 1 was used, namely, a static treatment that consists of a piston injector to feed $CO_2$ at the experimental pressure (1,000 or 3,000 psi) into a pressure vessel containing one gram of wet yeast cells. The vessel was immersed in a thermostated water bath to maintain at a constant temperature (25° or 35° C.). After yeast cells in the vessel were exposed to $CO_2$ for a designated length of time, $CO_2$ was released and the yeast cells were collected for subsequent assays of total protein and enzyme activities, as described in Example 1. In the experiments of repeated release of applied $CO_2$ pressure in the midst of an experimental run, $CO_2$ was recharged into the vessel at the experimental pressure immediately after it was released. The operation was repeated more than once in some experiments with a time interval that was divided evenly over the duration of a complete run.

Results and Discussion

Figure 6:
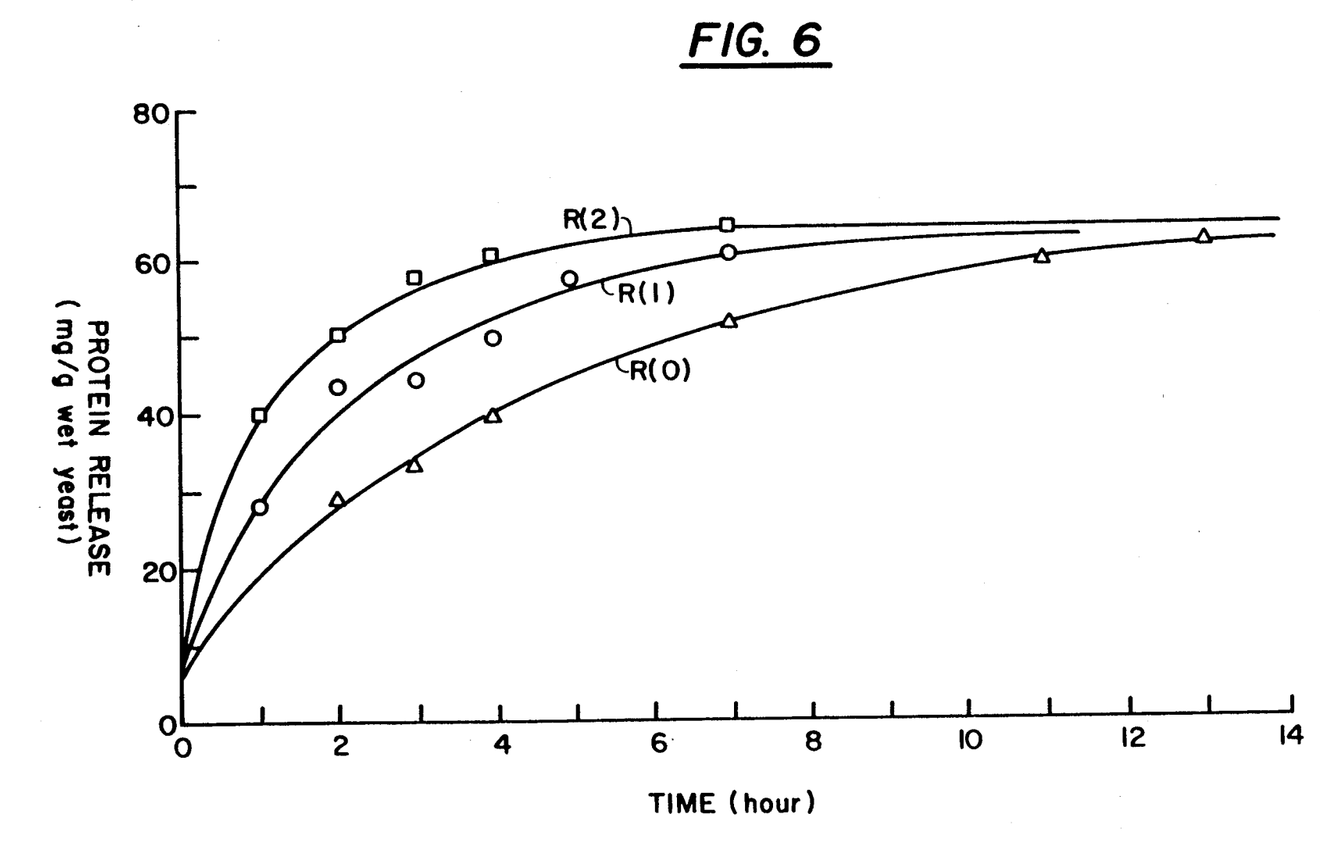
FIG. 6 shows a series of curves for protein release over exposure time to carbon dioxide for R(0), control, R(1) treated once and R(2) treated twice, to demonstrate the release of total proteins from yeast cells as a function of repeated release of fluid pressure at 35° C. and 1,000 psi.
Figure 7:
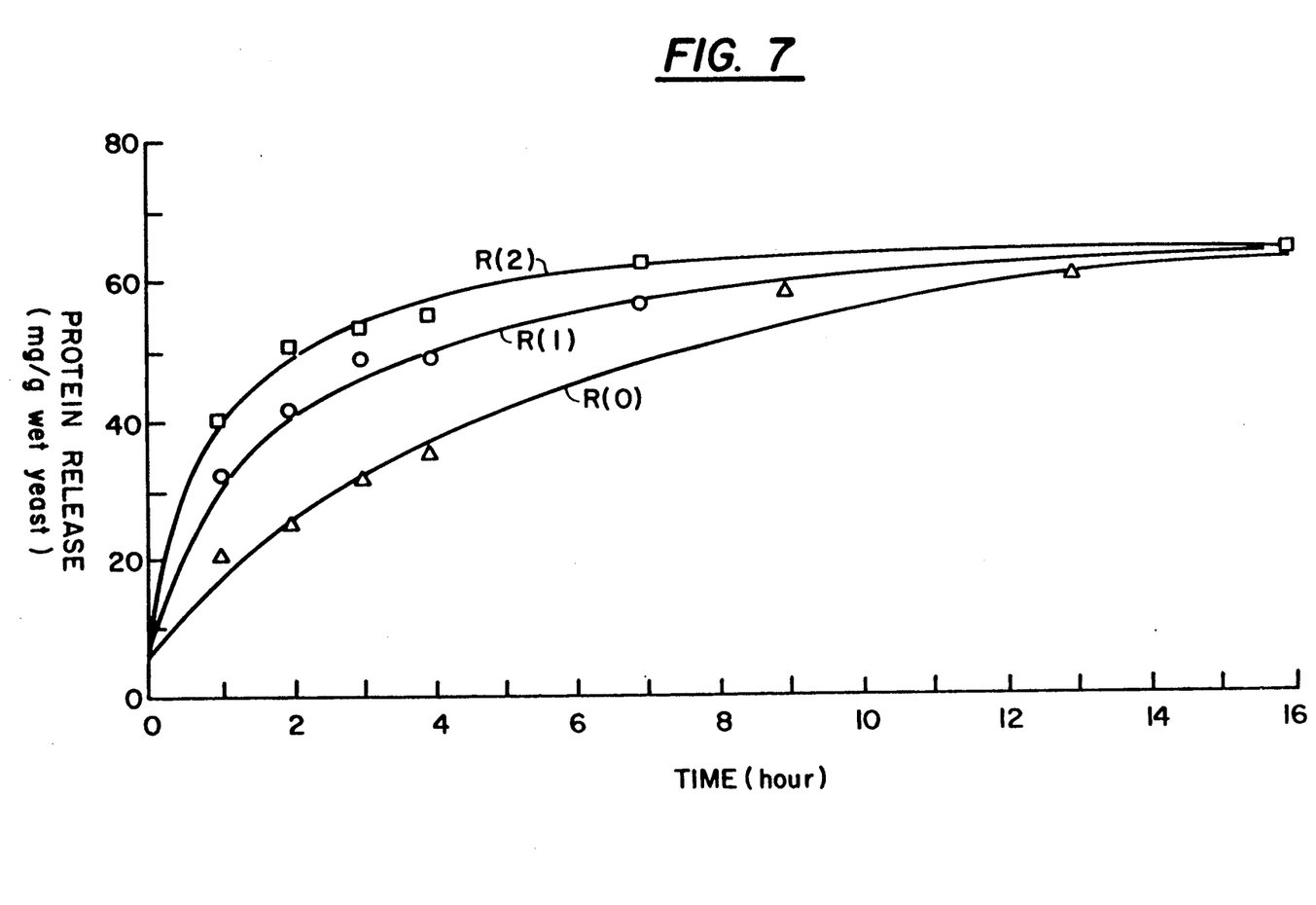
FIG. 7 shows the same set of curves as in FIG. 1 for release of total proteins from yeast cells as a function of repeated release of fluid pressure at 25° C. and 1,000 psi.
Figure 8:
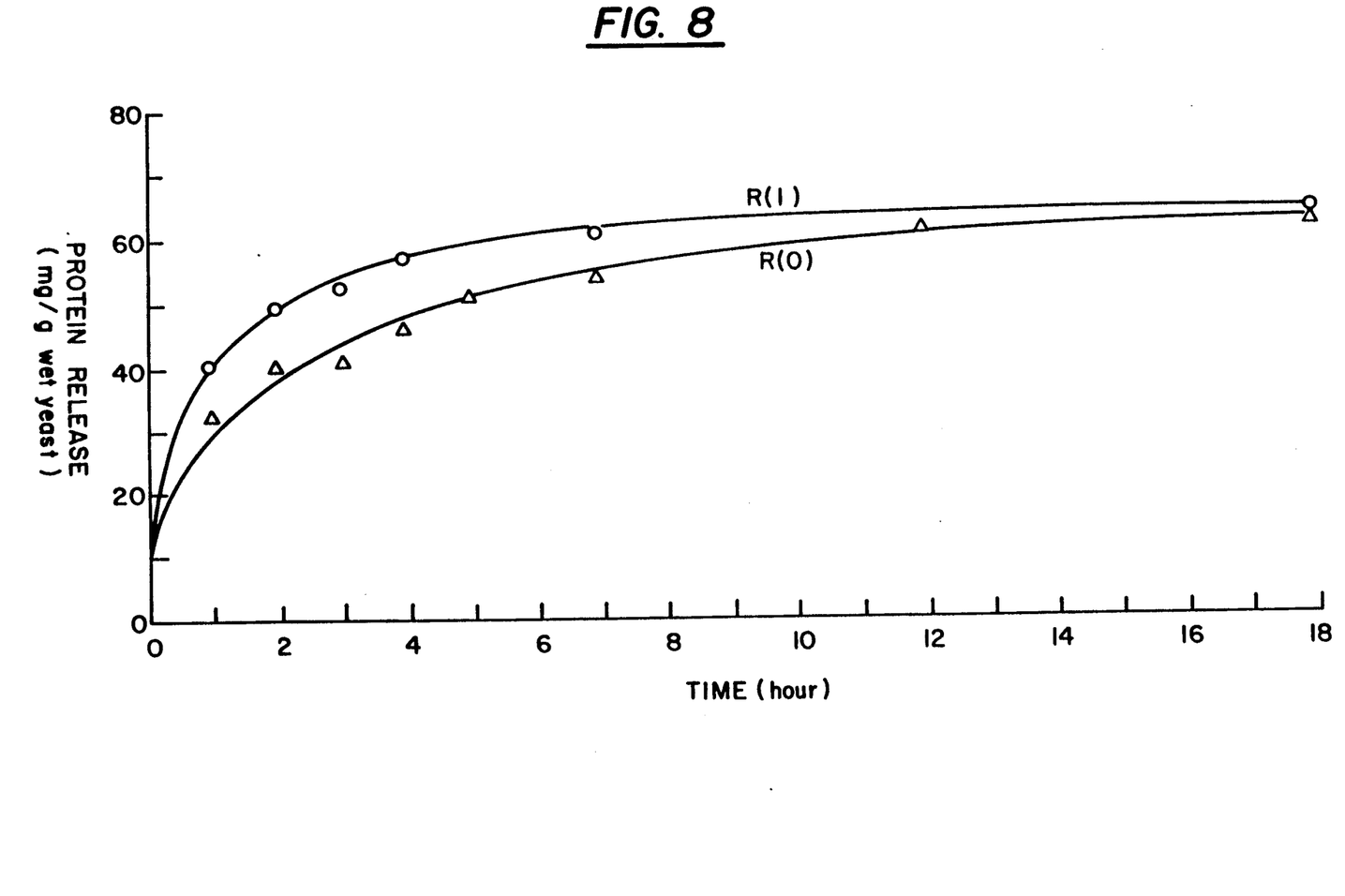
FIG. 8 shows the first two of curves as in FIG. 1 for release of total proteins from yeast cells as a function of release of fluid pressure at 35° C. and 3,000 psi.
Figure 9:
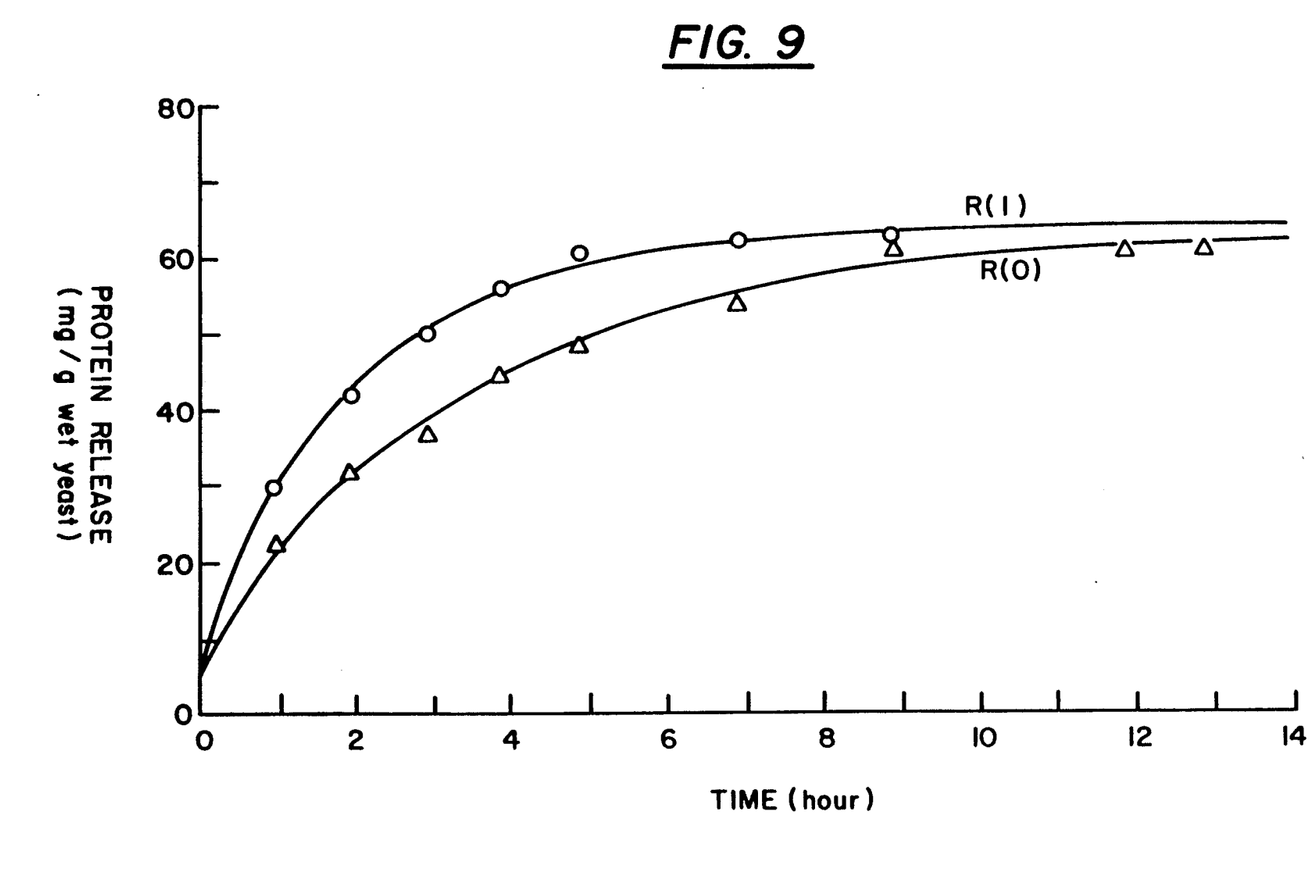
FIG. 9 shows the same set of curves as in FIG. 3 for release of total proteins from yeast cells as a function of release of fluid pressure at 25° C. and 3,000 psi.

Experimental results were obtained at both regions of supercritical and subcritical temperatures of $CO_2$ for comparison. FIG. 6 shows the release of soluble proteins as a function of exposure time to $CO_2$ at 35° C., while FIG. 7 presents similar results at 25° C. Both are under pressure of 1,000 psi. R(2) and R(1) in the figures denote that carbon dioxide was released and repressurized twice and once, respectively, in the midst of a complete disruption process. R(0) serves as a control operation. The improvement in disruption rates with repeated release of applied $CO_2$ pressure is evident. Similar results were observed at 3,000 psi, as shown in FIGS. 8 and 9. FIG. 8 is at 35°, FIG. 9 at 25° C.

The disruption rates are sensitive to process temperature and pressure. An increase in temperature and/or pressure will facilitate penetration of $CO_2$ into cells. Higher temperatures appear to enhance the transfer rate of $CO_2$, and also relax the cell walls to ease the penetration. Cell breakage comes as a result of gas expansion within the microbial cells when the vessel pressure is suddenly released. The action is strengthened under higher pressures. Another effective means to reduce the resistance of microorganisms to disruption is by addition of cell lytic enzymes as entrainers to $CO_2$ fluid. The operation of repeated release of fluid pressure can be used in combination with lytic enzymes to further improve the efficiency of cell disruption without deactivation of enzymes. Activities of various enzymes (alcohol dehydrogenase, invertase, glucose-6-phosphate dehydrogenase, and fumarase) in the ruptured cell suspension were assayed to ensure that the process preserved the functional properties of proteins in the presence of $CO_2$. The results are very similar to those presented in Example 1.

While the invention has been described in connection with what is presently considered to be the most practical and preferred embodiments, the invention is not limited to the disclosed embodiments but, on the contrary, is intended to cover various modifications and equivalents included within the spirit and scope of the following claims.

We claim:

1. A method to rupture microbial cells in order to recover intracellular materials in said cells comprising
   a) treating said cells with a lytic enzyme selected from the group consisting of $\beta$-glucuronidase, lysozyme, glucanases and mixtures thereof in conjunction with carbon dioxide under pressure of from above 500 psi (gauge) to about 5,000 psi so that said carbon dioxide will enter said cells and for a time of from between about one hour and about fifteen hours and a temperature of from about 10° to about 85° C. to allow enough carbon dioxide into said cells to effect later rupture then,
   b) suddenly releasing the applied fluid pressure on said cells so that the outer wall or membrane of said cells is ruptured by expansion of said carbon dioxide within said cells,
   c) repeating said steps a) and b) at least once,
   d) separating the remaining intracellular materials of step c), and
   e) recovering said intracellular materials, wherein said enzyme remains active and protein in said cells retains its native state in the ruptured cell suspension.

2. The method of claim 1 wherein said carbon dioxide contains an entrainer to enhance the rupture rate.

3. The method of claim 2 wherein said entrainer is selected from the group consisting of sulfur oxide, nitrogen monoxide, chlorolene, hydrogen peroxide, ethanol and mixtures thereof.

4. A method to rupture yeast cells in order to recover intracellular materials in said cells comprising
   a) treating said cells with a lytic enzyme selected from the group consisting of $\beta$-glucuronidase, lysozyme, glucanases and mixtures thereof in conjunction with carbon dioxide under pressure of from above 500 psi (gauge) to about 5,000 psi so that said carbon dioxide will enter said cells and for a time of from between about one hour and about fifteen hours and a temperature of from about 10° to about 85° C. to allow enough carbon dioxide into said cells to effect later rupture then,
   b) suddenly releasing the applied fluid pressure on said cells so that the outer wall or membrane of said cells is ruptured by expansion of said carbon dioxide within said cells,
   c) separating the remaining intracellular materials of step b), and
   d) recovering said intracellular materials, wherein said enzyme remains active and protein in said cells retains it native state in the ruptured cell suspension.

5. The method of claim 4 wherein said steps a) and b) are repeated at least once.

* * * * *